United States Patent [19]
Harris et al.

[11] Patent Number: 5,987,961
[45] Date of Patent: Nov. 23, 1999

[54] APPARATUS AND METHOD FOR TESTING PAVING

[76] Inventors: Jeffrey A. Harris, 2231-D #1 Centennial Rd.; Tamara K. Harris, 6321 N. Old Hwy., both of Salina, Kans. 67401

[21] Appl. No.: 09/176,306

[22] Filed: Oct. 22, 1998

[51] Int. Cl.[6] .................................................. G01L 5/00
[52] U.S. Cl. .................................. 73/11.01; 73/7; 73/38; 73/866
[58] Field of Search .................................. 73/7, 11.01, 38, 73/204.23, 215, 54.01, 54.03, 865.6, 866; 702/34

[56] References Cited

U.S. PATENT DOCUMENTS

| | | | |
|---|---|---|---|
| 3,431,776 | 3/1969 | Hughes | 73/146 |
| 3,459,038 | 8/1969 | Swift | 73/146 |
| 3,854,328 | 12/1974 | Schmidt | 73/146 |
| 3,888,118 | 6/1975 | Nims | 73/105 |
| 4,788,859 | 12/1988 | Khattak | 73/146 |
| 4,938,055 | 7/1990 | Tsuda | 73/146 |
| 5,036,709 | 8/1991 | McRae | 73/841 |
| 5,365,793 | 11/1994 | Terrel et al. | 73/813 |

FOREIGN PATENT DOCUMENTS

| | | |
|---|---|---|
| 568559 | 10/1975 | Switzerland . |
| 1377321 | 2/1988 | U.S.S.R. . |
| 2067769 | 7/1981 | United Kingdom . |

Primary Examiner—Hezron Williams
Assistant Examiner—Thuy Vinh Tran
Attorney, Agent, or Firm—Richard C. Litman

[57] ABSTRACT

An apparatus for testing asphalt or other paving samples includes a cabinet for housing the mechanical elements of the invention, and a computerized control console for monitoring and controlling the mechanism. The cabinet includes a pair of weighted rollers or wheels, which are driven reciprocatingly over a corresponding pair of pavement samples placed in trays beneath the wheels. The trays in turn rest in a water bath contained in an open water tank within the cabinet. The water may be heated to a predetermined temperature as desired, for providing the effects of high heat and moisture during testing. Each roller arm is in contact with a linear value displacement transducer, which measures the wear of each sample several times during each roller stroke. Lifting devices are also provided to lift the subject roller arm if one of the samples breaks down prematurely, in order to avoid premature abandonment of the testing of the second sample. All of the electromechanical components and their functions are controlled and/or monitored by a computer, which controls the speed of the wheel or roller drive motor, the temperature and circulation of the water bath, monitors the wear of each pavement sample according to the corresponding displacement transducer, and controls the lifting of either roller arm in the event of the breakdown of one of the samples. The computer and monitor are installed with a cabinet which houses various electrical components which in turn monitor and control the various elements of the sample test cabinet.

18 Claims, 5 Drawing Sheets

APPARATUS AND METHOD FOR TESTING PAVING

BACKGROUND OF THE INVENTION

1. Field of the Invention

The present invention relates generally to devices and methods for testing the durability of various materials, and more specifically to a machine and method for testing paving. The machine applies a rolling pressure to one or more pavement samples (e. g., asphalt) held in a tray within the machine. A hot water bath is also applied to the sample(s) in order to accelerate the effects of moisture and humidity thereon.

2. Description of the Related Art

The paving of roads, highways, parking areas, etc., has become an important part of our transportation system throughout the nation. Asphalt is by far the most commonly used paving medium used, with other materials (concrete, etc.) also being used. Initially, asphalt was made by mixing virtually any grade of tar or similar weight and viscosity petroleum product with sand, gravel, etc. This is still the basic method of forming asphalt paving material, but much has been learned about the quality of different ingredients therein and the proportions of materials which are used in the formation of asphalt paving.

Asphalt paving made from inferior ingredients, or in improper proportions, will not hold up as well as more carefully formed asphalt mixes. Also, different conditions require different mixes for optimum durability. Accordingly, various means have been developed in the past for testing asphalt and other paving materials. Most of these testing means utilize some form of test equipment installed on a road vehicle of some sort, with the vehicle then being driven over the subject paving area for testing. This has at least a few disadvantages in comparison to testing samples in a controlled environment in the laboratory. First, a relatively large expanse of pavement must be applied in order to provide a sufficient area over which a motor vehicle may be driven. Second, the environment of the test cannot be controlled when the paving is applied in an outdoor environment, as the environment is subject to heat, cold, rain, snow, etc. Third, in all likelihood such paving is subject to other traffic in addition to the test vehicle, with the other traffic comprising numerous vehicles of widely varying weights and speeds. Controlled testing in such conditions, and achieving consistent results, is all but impossible.

Accordingly, a need will be seen for a paving test machine and method capable of testing various samples of asphalt or other paving under tightly controlled conditions of temperature and humidity in an indoor laboratory environment. The machine accepts one or more paving samples and applies a repeated rolling pressure to the samples for a predetermined period of time or number of cycles, or until breakdown occurs. The machine provides precise measurements of the wear of the paving during testing, and automatically shuts off any one sample test if excessive wear occurs before all testing is complete. The machine is operated by computer control, and results are provided by the computer for later evaluation. A hot water bath may also be applied to the sample(s) in order to accelerate the effects of temperature and humidity on the sample(s).

A discussion of the related art of which the present inventor is aware, and its differences and distinctions from the present invention, is provided below.

U.S. Pat. No. 3,431,776 issued on Mar. 11, 1969 to George W. Hughes, titled "Road Surface Testing Device," describes a fifth wheel device applied to a motor vehicle and riding against the underlying surface. The fifth wheel is equipped with a brake, with the brake being applied when the vehicle is decelerating. The amount of braking pressure required before lockup of the wheel occurs, provides a measure of the surface friction of the underlying paving or other material. The Hughes device may be useful in testing the friction coefficient on airport runways and the like, but provides no information whatsoever relating to the durability or wear resistance of the paving, nor can the device provide a consistent test of a relatively small sample, as can the present invention.

U.S. Pat. No. 3,459,038 issued on Aug. 5, 1969 to Gilbert Swift, titled "Apparatus For Testing Road Surfaces And Method," describes a means for testing the roughness of a road surface. The means includes a fifth wheel secured to a motor vehicle, and a system for measuring the vertical motion of the wheel per unit of horizontal travel over a surface. The Swift apparatus and method do not provide for repetitive motion over a surface to measure the wear of that surface, nor does the Swift apparatus and method provide for the testing of a small sample in a controlled environment, as provided by the present invention.

U.S. Pat. No. 3,854,328 issued on Dec. 17, 1974 to Robert J. Schmidt, titled "Resiliency Testing Device," describes a fixture in which a sample may be placed for testing. The device applies a periodic compression to the subject material, with the material being rotated 90 degrees after a predetermined number of cycles for further testing. While the test sample may be placed in water, as in the present invention, the Schmidt device only applies a direct compressive load, with no rolling lateral load being applied to increase the pressure relatively gradually across the sample to simulate wear more accurately due to vehicle tires. Moreover, the Schmidt device is only capable of testing a single sample at a time, and Schmidt does not provide any means for automatically terminating the test when a predetermined wear or compression limit of the sample is reached, as provided in the present invention.

U.S. Pat. No. 3,888,118 issued on Jun. 10, 1975 to Jerry R. Nims, titled "Method And Apparatus For Determining Road Roughness," describes a device installed in a motor vehicle for testing the roughness of a surface over which the vehicle is driven. The device comprises a transducer and recorder installed in some spring suspended portion of the vehicle, and a cable connected to an unsprung portion of the vehicle. As the vehicle is driven over a surface, any irregularities will result in the unsprung and spring suspended portions of the vehicle moving relative to one another, with the cable actuating the transducer to produce a recording of the degree of roughness. No means of measuring pavement wear is disclosed by Nims, nor is any means of measuring the wear of a sample in closely controlled conditions disclosed, as provided by the present invention.

U.S. Pat. No. 4,788,859 issued on Dec. 6, 1988 to Anwar S. Khattak, titled "Method And Apparatus For Determining Deflection In Pavement," describes an optical device placed in a vehicle and driven across the paved area subject to measurement. Obviously, no wear can be applied to the paved area by an optical testing means, which merely measures existing roughness or unevenness, rather than applying a weight to produce wear to a sample, as in the present invention. Also, the Khattak device and method cannot be applied to a relatively small sample in a machine in a controlled laboratory environment, as provided by the present invention.

U.S. Pat. No. 4,938,055 issued on Jul. 3, 1990 to Isami Tsuda, titled "Apparatus For Testing Abrasion," describes a device having a rotary turntable upon which paving samples are placed, with a grinding wheel, e. g., studded tire, rotating about a fixed axis. The rotation of the wheel causes the turntable to rotate, thereby periodically rotating the sample (s) beneath the wheel. Tsuda also provides a series of temperature control chambers opposite the wheel, through which the sample(s) is/are passed periodically. The present invention is constructed essentially opposite the Tsuda device, with the paving sample(s) being fixed in one or more trays, and the wheel(s) reciprocating linearly back and forth across the sample(s). Also, it is noted that Tsuda cannot provide continuous environmental conditions (heat, cold, etc.) for his samples, as they only periodically pass through the stationary environmental areas, and are clear of those areas when in contact with the abrasive wheel. The present invention provides continuous application of water at a predetermined temperature in order to apply such environmental influences continually during the test.

U.S. Pat. No. 5,365,793 issued on Nov. 22, 1994 to Ronald L. Terrel et al., titled "Equipment And Method For Environmental Testing Of Bituminous Specimens," describes a test cell in which a single sample core is placed, with a load cell providing periodic pneumatic compressive force to the sample. The test cell may be provided with water to alter the test environment. The Terrel et al. device does not apply a linear, reciprocating rolling force to the sample, as in the present invention.

Swiss Patent Publication No. 568,559 published on Oct. 31, 1975 to Jean-Claude Gressin illustrates a framework which may be secured beneath a vehicle (e. g., a truck) for measuring the roughness or unevenness of the underlying pavement or surface. The device is not applicable for use in a laboratory environment under controlled conditions, nor does the device produce and measure wear in a sample by providing a continuous reciprocating and rolling force to the sample, as in the case of the present invention.

British Patent Publication No. 2,067,769 published on Jul. 30, 1981 to Bergougnan-Benelux, titled "Measuring Static And Dynamic Material Characteristics," describes a device for imparting compressive force to a resilient material, e. g., rubber or the like. A relatively small spherical impression body is oscillated against the test sample over a relatively short distance. No means of rolling a movable test roller horizontally over the surface of a test article is disclosed in the British Patent Publication, nor is any means provided for adjusting moisture or humidity in the environment of the sample, as provided by the present invention.

Finally, Soviet Patent Publication No. 1,377,321 published on Feb. 29, 1988 illustrates a mechanical strain gauge linkage. The linkage is not suitable for imparting a force to a test sample, but only for measuring a deflection. No means for imparting a rolling force, nor for altering the moisture content of the sample environment, is evident in the Soviet Patent Publication.

None of the above inventions and patents, either singly or in combination, is seen to describe the instant invention as claimed.

SUMMARY OF THE INVENTION

The present invention comprises an apparatus and method for testing the durability and wear characteristics of an article, such as asphalt paving or the like. The apparatus comprises an outer cabinet with an inner water tank therein. The inner tank includes a pair of removable sample trays, for containing asphalt or other samples therein. The water tank provides water at a predetermined temperature, at least slightly over the top(s) of any sample(s) contained therein. A pair of horizontally reciprocating arms each include a weighted wheel or roller thereon, with an electric motor providing reciprocating power for the arms and wheels. The rollers are thus rolled back and forth across the samples within the trays, with means being provided for measuring wear of the samples by detecting the amount of vertical settling of the arms guiding the wheels as they settle into the samples during testing. A means is provided for slightly lifting either of the two arms in the event that the corresponding sample fails, in order that the opposite arm and sample test may continue. The present invention also includes an appropriate computer, interface, and programming for operating the above described machine, and for controlling water temperature and other parameters and recording the results of testing.

Accordingly, it is a principal object of the invention to provide an improved apparatus for testing paving or other sample material, comprising a machine having one or more horizontally reciprocating wheels or rollers therein for imparting a rolling force to corresponding samples.

It is another object of the invention to provide an improved apparatus including water bath means for the samples contained therein, for submerging such samples in water at a predetermined temperature.

It is a further object of the invention to provide an improved apparatus including means for at least slightly lifting either of the wheels or rollers from the sample in the event that one of the samples fails, in order to continue testing of the second sample without disrupting the entire testing process.

An additional object of the invention is to provide an improved method of testing asphalt samples or the like, including using a computer and appropriate interfaces and programming for controlling the apparatus and for recording the test results.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
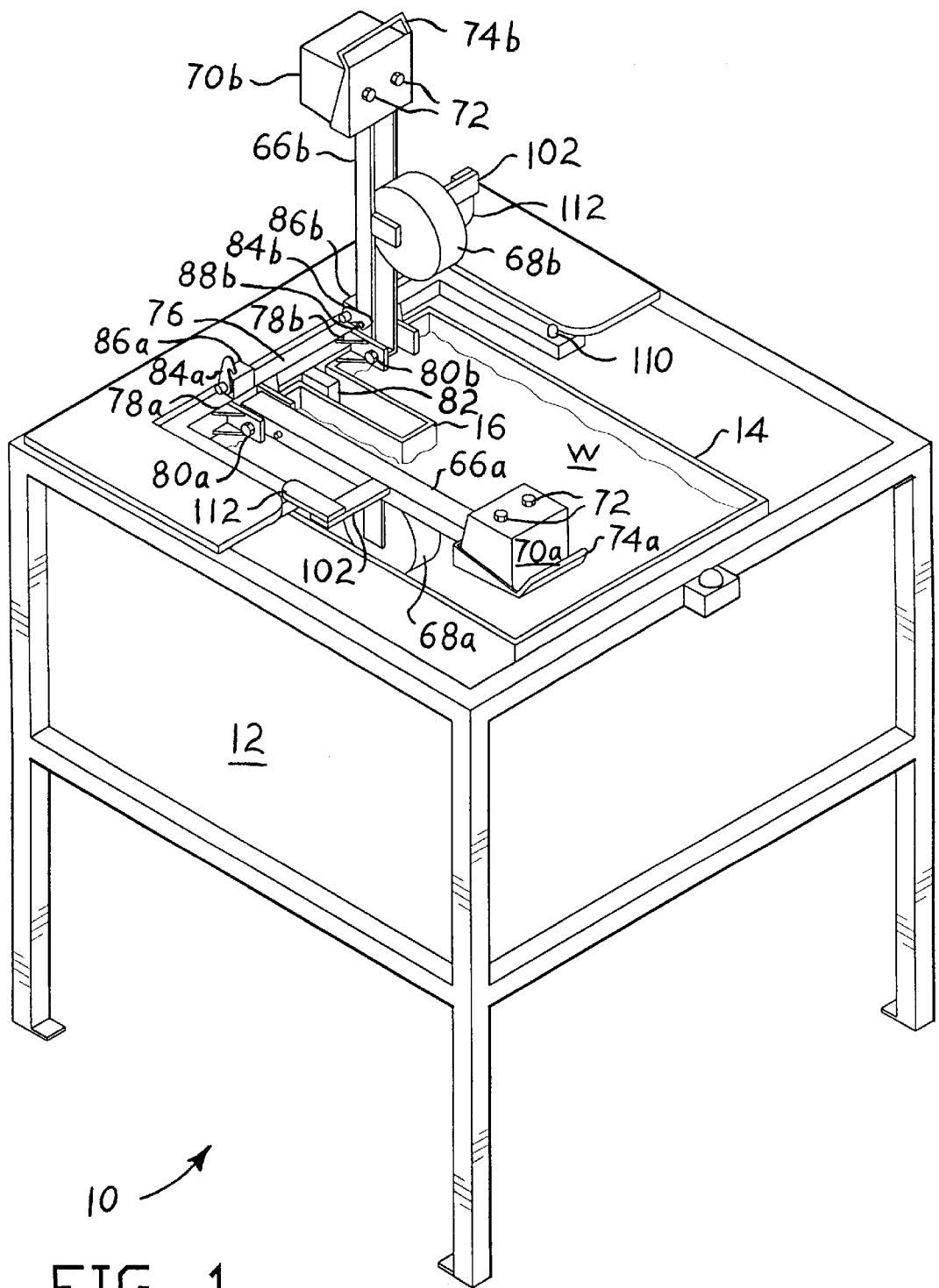
FIG. 1 is a perspective view of the present paving test machine, showing its general configuration and features.

The present invention comprises an apparatus for testing the durability of paving samples, with the apparatus or machine being indicated by the reference character 10 throughout the drawings. The present disclosure also describes a method of testing paving samples using the present invention. FIG. 1 provides an overall perspective view of the present paving testing machine 10, showing various components and features thereof. The apparatus of the machine 10 is housed in a stationary cabinet 12, which may be positionally fixed as desired in the laboratory or test facility; the present machine 10 does not move over an area of paving, as in the case of various vehicle mounted test devices of the prior art.

The cabinet 12 includes a water tank 14 therein, with the tank 14 having a rear slot 16 formed therein for clearance of the roller mechanism drive arm, discussed further below. The tank 14 also includes means for securing at least one, and preferably two, removable pavement sample trays 18a and 18b therein, shown in FIG. 2. It will be understood that additional sample trays, and corresponding pavement test mechanisms as described further below, may be incorporated in the present paving test invention, if so desired. The two trays 18a and 18b include handles 20 extending therefrom, with tray hold down means 22 (wing nuts and bolts, etc.) provided in the water tank 14 about the peripheries of the trays 18a and 18b for securing them immovably within the water bath W during paving sample test operations. The trays 18a and 18b are placed within the water tank 14 with their upper surfaces, including any paving samples P1 and P2 placed therein, completely submerged beneath the surface of the water W in the tank 14.

Figure 2:
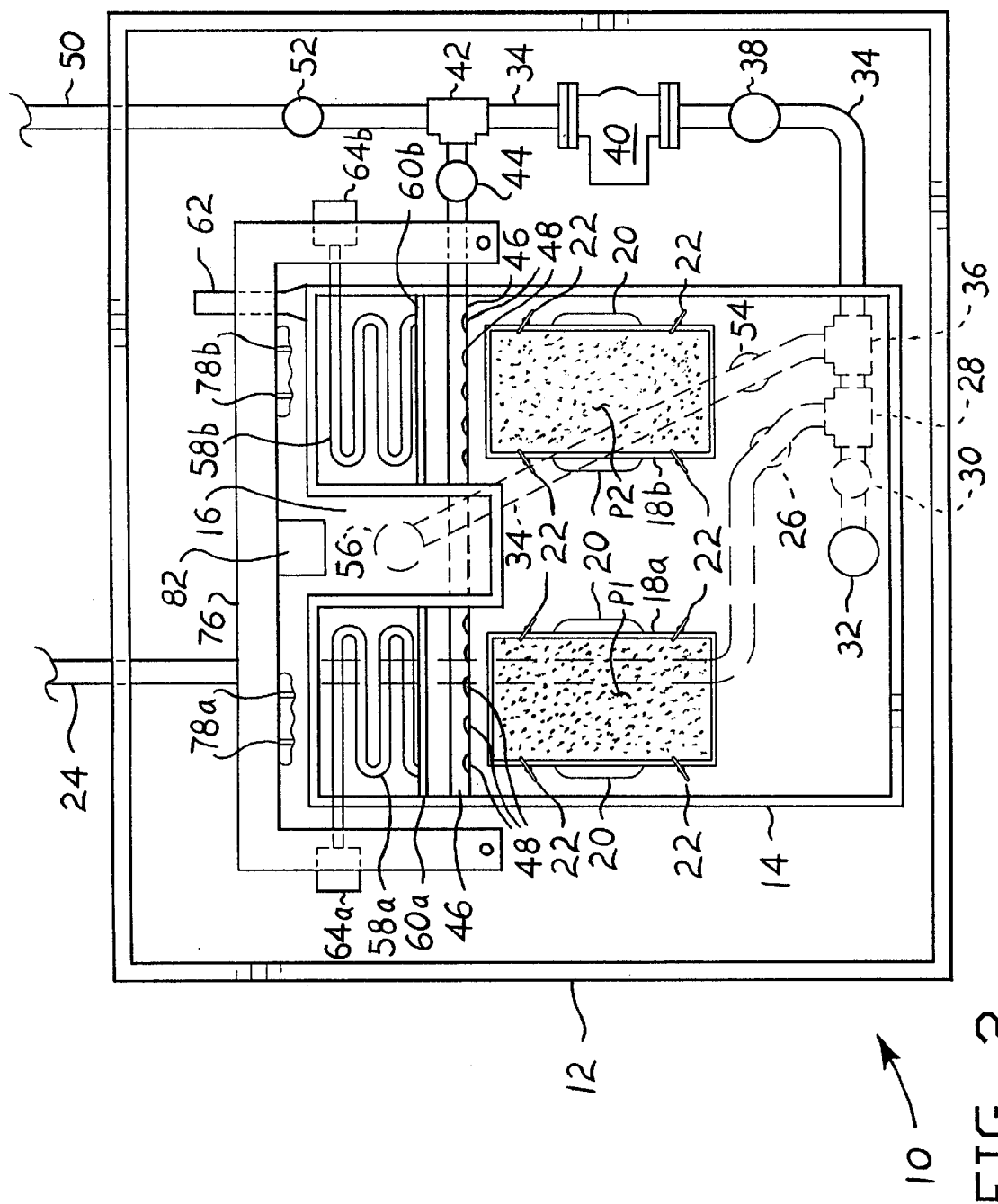
FIG. 2 is a top plan view of the water tank, paving trays, and water heating and circulation apparatus of the present machine.

FIG. 2 illustrates the general layout of the heating, temperature control, and circulation means for the water bath W contained within the water tank 14 of the machine 10. (It will be noted that much of the water supply and circulation system is shown in broken lines, as it would be beneath the tank 14 in the top plan view of FIG. 2.) A water inlet or supply line 24 enters the machine 10 at the back of the cabinet 12 and continues to a water inlet and fill valve 26, for controlling the amount of water used to fill the tank 14. (A tee, not shown, may be provided for connecting a wash down hose to the inlet line 24, if so desired.)

The water inlet line 24 extends beyond the inlet and fill control valve 26 to a tee fitting 28, with one side of the tee 28 extending to a tank drain control valve 30 and thence to the tank drain 32. The opposite side of the tee 28 extends to the water circulation return line 34, via another tee fitting 36. The circulation and return line 34 passes through a filter 38, with the water being circulated by a pump 40. A third tee fitting 42 allows the water to pass to a tank fill and run valve 44, and thence to a water tank distribution line 46 having a plurality of water outlet passages 48 therein, for passing the water into the tank 14. (The center portion of the distribution line 46 passes beneath the arm clearance slot 16 in the tank 14, which is formed in only the upper portion of the tank 14 to provide the required arm clearance.) The opposite side of the tee fitting 42 extends to a water outlet line 50, via a drain valve 52. water distributed via the distribution line 46 is recirculated back through the circulation and return line 34 via a water draw valve 54 and pickup 56 beneath the arm clearance slot 16, with the valve 54 being open during operation of the system.

A heating element, respectively 58a and 58b, is provided at the back of the tank 14 to each side of the arm clearance slot 16. Water fills the front of the tank 14 and flows over a pair of weirs, respectively 60a and 60b, where it circulates about the respective heater elements 58a and 58b and back through the pickup 56 to be recirculated through the tank 14. An overflow pipe 62 is provided at the back of the tank 14.

The two heating elements 58a and 58b are controlled by respective control means 64a and 64b, which may be conventional silicon controlled rectifiers (SCRs) or other suitable control means as desired. Preferably, the water is maintained at a constant temperature according to the goals of the test operation, with the selected temperature preferably ranging from zero to eighty degrees Celsius. (The circulation system keeps the water in motion to prevent freezing, so long as the temperature does not drop appreciably below freezing.) Other temperature ranges may be used if so desired. The controllers 64a and 64b, as well as the water circulation through the above described system, are controlled by computer means described in general further below.

When a test run is to be made, the tank 14 is filled by opening the inlet valve 26, while confirming that the tank drain control valve 30 and drain valve 52 are closed and the tank fill and run valve 44 is open. Water is circulated by the pump 40 through the fill and run valve 44 to the distribution line 46, and thence into the forward portion of the tank 14. The water is maintained at an appropriate depth for covering the paving samples P1 and P2 by the weirs 60a and 60b, with water flowing over the weirs to circulate about the heater elements 58a and 58b. After heating, the water circulates back through the pickup 56 and return line 34, to pass through the filter 38 and be pumped back through the system by the pump 40.

The present machine 10 also includes weighted rollers and drive means therefor, for applying a continuous weighted rolling action to each of the paving samples P1 and P2 which have been placed within the water bath W of the machine 10. One of the roller and drive means is shown in detail in FIG. 3, with both rollers and drive arms being shown more generally in FIG. 1. The roller mechanisms basically comprise a pair of pivotally mounted arms, respectively 66a and 66b, with a roller, respectively 68a and 68b, mounted to each of the arms. (The arms and rollers are removed in FIG. 2, for showing clearly the water heating and circulation system in that drawing Figure.)

Rollers 68a and 68b are positioned below their respective arms 66a and 66b when the arms are lowered to their generally horizontal operating positions, shown by the arm 66a and roller 68a of FIGS. 1, 3, and 4. Each arm 66a and 66b has a distal end including a weight, respectively 70a and 70b, removably secured thereto. The weights 70a and 70b produce a greater downforce on their respective rollers 68a and 68b, to accelerate the effects of wear and tear on the paving samples P1 and P2. Preferably, sufficient weight is provided to produce about 158 pounds of force on each roller 68a and 68b, but the weights 70a and 70b may be adjusted as desired. The weights 70a and 70b are held securely in place on the distal end of each respective arm 66a and 66b, by appropriate fasteners (e.g., bolt and nut assemblies 72). A handle, respectively 74a and 74b, may be provided on the distal end of each of the arms 66a and 66b for manually lifting the arms as required.

Each of the arms 66a and 66b is pivotally mounted to the central crossmember of a generally U-shaped slider frame 76 by means of a gusseted bracket, respectively 78a and 78b, and pivot pin or bolt, respectively 80a and 80b, to each side of the attachment end of each arm 66a and 66b. The two arms of the frame 76 are mounted on conventional slider bearings (not shown) to allow the frame 76, and arms 66a and 66b attached thereto, to reciprocate horizontally forwardly and rearwardly over the top rear of the tank 14. A generally vertical connector arm 82 extends downwardly from the central portion of the slider frame 76, serving to drive the slider frame 76 and its attached roller arms 66a, 66b and corresponding rollers or wheels 68a, 68b back and forth over the paving samples P1 and P2 within their respective trays 18a, 18b. The slot 16 formed in the upper rear of the water tank 14 provides clearance for the connector arm 82 as it reciprocates.

Each of the arms 66a and 66b may be lifted to a generally vertical position (or slightly past vertical, to balance the weight 70a or 70b installed thereon) as desired, in order to install and remove the paving sample trays 18a, 18b, perform maintenance on the machine 10, etc., as required. Each of the arms 66a, 66b is held in its raised position by a catch, respectively 84a and 84b, affixed to a block, respectively 86a and 86b, which is in turn affixed to the lateral portion of the slider frame 76. A lateral pin 88a and 88b extends from each respective arm 66a and 66b to be captured by a respective catch or latch 84a, 84b when the arm(s) is/are raised, as shown by the raised arm 66b of FIG. 1.

Figure 3:
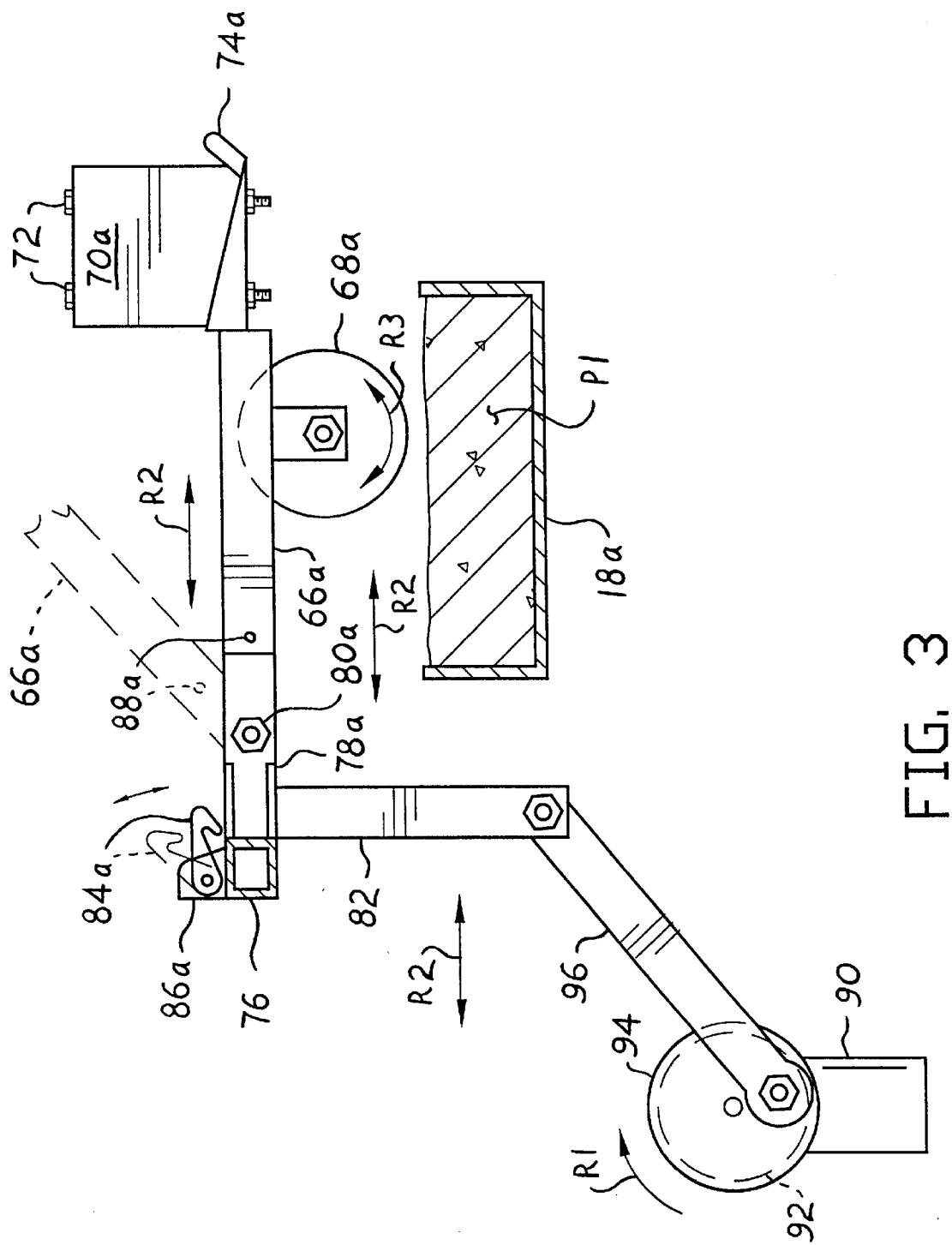
FIG. 3 is a side elevation view of the rotating apparatus and one of the reciprocating components of the present machine.

FIG. 3 provides a side elevation view of the drive means for the connector arm 82 and its attached slider frame 76, roller arms 66a and 66b, and rollers 68a and 68b. An electric motor 90 drives a right angle speed reduction drive 92, which in turn rotates a crank wheel 94. A connecting rod 96 is connected eccentrically to the crank wheel 94 and to the lower end of the connector arm 82, serving to translate the rotary motion of the crank wheel 94, indicated by the rotary arrow R1, to the reciprocating motion of the connector arm 82, slider frame 76, and roller arms 66a and 66b, indicated by the reciprocating arrows R2, resulting in the rolling of the rollers 68a, 68b over the paving samples P1 and P2, as indicated by the rolling arrow R3 in FIG. 3. The motor 92 is governed by a drive speed controller (shown generally in the schematic diagram of FIG. 5), which allows the reciprocating speed to be varied from about 36 to 70 cycles per minute. Slower or faster rates may be provided, if so desired.

As the above described machine 10 repeatedly rolls rollers or wheels 68a, 68b over the respective paving samples P1 and P2, the samples will gradually be worn away, depending upon the temperature of the water bath, quality of the sample, roller speed and pressure, and perhaps other factors. Accordingly, the present machine includes means for detecting such sample wear, and also for automatically lifting at least slightly either of the arms 66a, 66b and their respective rollers 68a, 68b independently of one another in the event of a catastrophic failure of a paving sample, in order that the test of the remaining sample not be interrupted.

Figure 4:
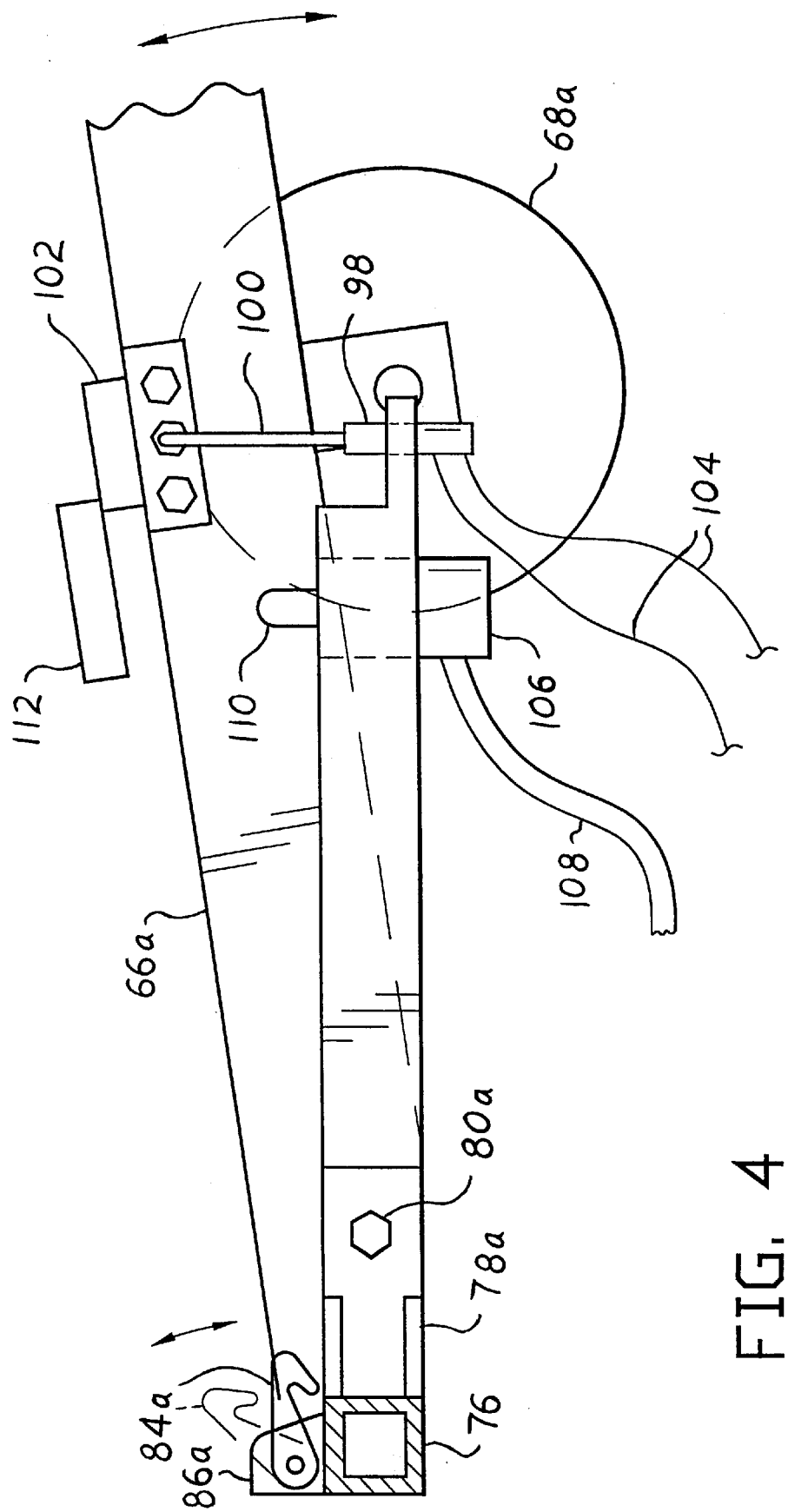
FIG. 4 is a side elevation view of the wear measurement means and automatic shutoff means of the present machine.

FIG. 4 provides an elevation view of the electromechanical and pneumatic components which respectively measure the wear of the sample and provide for the partial lifting of the arm as required. A paving sample wear detector 98 is installed at the distal end of each of the lateral arms of the generally U-shaped sliding frame 76, with the detector including an extended pin 100 which bears against a contact plate 102 which extends laterally from the arm, e. g., arm 66a in FIG. 2. Preferably, the wear detector 98 comprises a conventional linear value displacement transducer (LVDT), which provides an electrical signal which changes in value in accordance with the position of the pin 100 relative to the detector 98 body. The electrical signals are passed to a computer system, shown schematically in FIG. 5, for processing, via electrical lines or wiring 104. As the paving sample gradually wears due to repeated reciprocating rolling passes thereover by the roller wheel, e.g., roller 68a of FIG. 4, the arm 66a is displaced lower and lower, with the contact plate 102 gradually pushing the contact pin 100 farther into the body of the LVDT 98, thereby changing the electrical signal output of the LVDT.

The present invention also provides for at least a slight lifting of each of the arms in the event of a sudden major failure of a paving sample during a test run, as noted further above. This permits the test run to continue with the unfailed sample, while relieving all pressure on the side containing the failed sample. Thus, the entire test need not be discontinued in the event of a single sample failure.

Automatic arm lifting means comprising a pneumatic cylinder 106 is provided in each lateral extension of the sliding frame 76, generally adjacent the LVDT sample wear detector 98 described above. The cylinder 106 is connected to a conventional pneumatic pressure source (air compressor, etc.) by a pneumatic line 108, and is controlled by the computer system of FIG. 5, described further below. If the LVDT 98 detects a sudden, major downward movement of the arm, e.g., arm 66a of FIG. 4, the resulting change in electrical value is transmitted to the computer via the electrical output lines 104, with the computer determining that such a major change is beyond normal parameters. The computer then provides a signal to the pneumatic pressure source, releasing pressure to the cylinder 106. This results in the raising of the lift pin 110, which bears against the secondary extension 112 of the arm 66a to automatically lift the extension 112 and thus the arm 66a and its roller 68a to relieve pressure on the failed paving sample.

Figure 5:
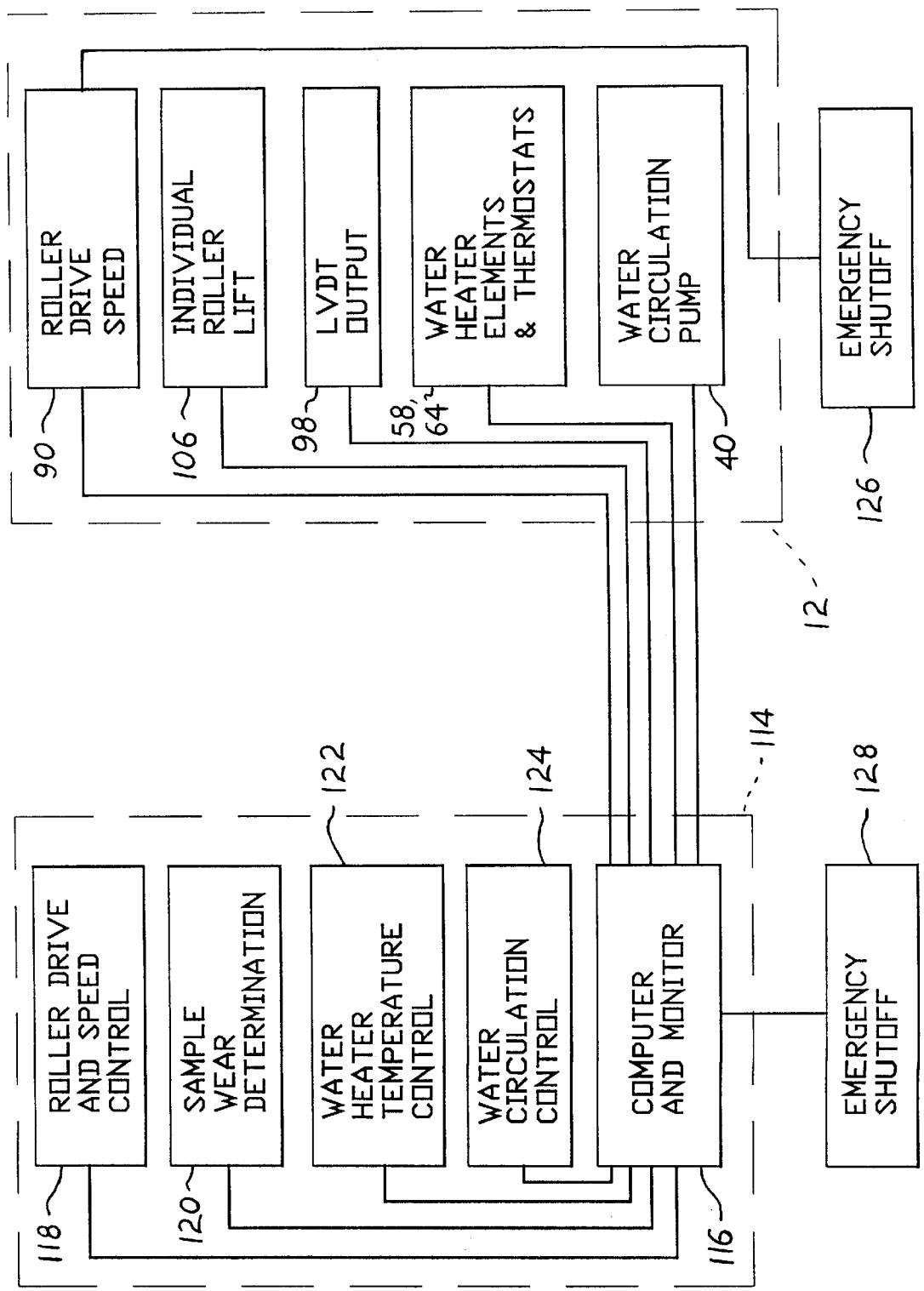
FIG. 5 is a schematic diagram of the basic componentry and control system of the present paving test machine.

As noted above, the present paving testing machine 10 is controlled by a computer system, with the basic system shown schematically in FIG. 5 of the drawings. The rectangular enclosure shown in broken lines to the right side of FIG. 5 represents the cabinet 12 of the present machine 10, and encloses all of the various components discussed in detail further above, i.e., roller drive speed motor 90 and conventional speed controls therefor, the automatic roller lifting means 106, LVDT wear detector and output 98, water heater elements 58 and their controls 64, and the water circulation pump 40 and associated plumbing.

The computer system of the present invention includes various electrical and pneumatic control systems housed on or in a cabinet 114, shown schematically by the broken line enclosure to the left side of the schematic drawing of FIG. 5. A computer system 116, e.g., a conventional small portable or personal computer and monitor which has sufficient capacity for controlling the various functions of the present machine, is programmed to provide such control and to provide a record of each test run accomplished.

The computer 116 includes roller drive and speed control means 118, such as appropriate programming, enabling an operator of the present machine to set the reciprocating speed, number of cycles, etc., as desired by using the computer 116. While the reciprocating speed would normally be programmed as a constant during the entire test duration, it will be noted that the computer control incorporated with the present invention enables the reciprocating speed of the rollers 68a, 68b to be varied over the course of a test run, if so desired.

The computer 116 is also detecting pavement sample wear during the test run, by means of the LVDT output 98 and appropriate programming for measuring sample wear and wear rate, as indicated by the sample wear determination means 120 of FIG. 5. As described further above, if the computer 116 and its sample wear determination means 120 detect a relatively rapid change in wear, indicating a breakdown or destruction of the sample, then the computer 116 sends a signal to the pneumatic roller lift 98 for the appropriate sample tray, lifting that arm and roller from the sample.

The computer 116 also controls the water temperature by means of a control program 122 for the water heaters 58a, 58b and their respective controllers 64a, 64b, shown in FIG. 2. Again, the water temperature would normally be programmed to maintain a constant value during the course of a test run. However, the present system enables the temperature to be varied during a run, to simulate diurnal changes in temperature, weather changes, etc., if so desired. The computer also controls the rate of flow of the water by means of the water circulation control system 124 which controls the rate of the pump 40, shown in FIG. 2.

The provision for lifting the weight of one or both of the rollers 68a and/or 68b from the paving sample(s) in the event of sudden failure of the sample(s), has been discussed in detail further above. However, it will be noted that the reciprocating movement of the two rollers 68a, 68b, their respective arms 66a, 66b, and the slider frame 76, will continue, even though one or both of the arms may have been partially lifted. The above process does nothing to shut down the operation of the entire machine in the case of an emergency, or for other reason. Accordingly, an emergency shutoff control 126 is provided in a conspicuous location at the front of the cabinet 12, for shutting off the drive motor 90 in the event that a rapid shutdown is required for any reason. This emergency shutoff control 126 could also be connected to the water heater elements 58a, 58b and/or the circulation pump 40, if so desired, to produce an immediate shutdown of all of the various major electrically powered components of the machine on demand.

In a similar manner, another emergency shutoff control 128 may be provided at the computer control console or cabinet, if so desired. In the event that the operator of the present machine was working at the computer console (entering data, programming a later run, etc.), he or she could instantly shut down the machine in the event of a serious problem. The shutoff control 128 may communicate through the computer 116 to signal the computer to shut down at least the roller drive and speed control 118, and perhaps also the water heater temperature control 122 and circulation control 124.

In summary, the present apparatus and method of testing paving samples provides a much needed means of consistently testing such samples, without the variations in test conditions which are usually experienced when using a vehicle and associated mobile test equipment traveling over a paved area. Testing using the present machine is also considerably less costly than using a moving vehicle, as (1) no large area need be paved for the test, and (2) the costs of operation of the present machine are considerably less than the cost of operation of a moving vehicle and test equipment.

The above described control systems 118 through 124, in combination with the computer 116, serve to monitor and control the test run of various paving samples being tested by using the present machine 10. Moreover, the computer 116 with its memory capacity, also serves to record and store sample wear of various paving samples recorded during a number of different test runs, for comparing the durability of such various samples.

The present machine, at least those components associated with the pavement sample test cabinet and water tank and bath, are preferably formed of corrosion resistant materials (e.g., stainless steel) insofar as possible, in order to resist the corrosive effects of the warm or hot water environment and to provide a durable and long lasting piece of equipment. Accordingly, the present paving test machine will be seen to provide a much needed advance in the state of the art of pavement testing, and will prove to be of great value in the field.

It is to be understood that the present invention is not limited to the sole embodiment described above, but encompasses any and all embodiments within the scope of the following claims.

We claim:

1. An apparatus for testing paving samples, comprising:
   a fixed, stationary cabinet;
   said cabinet including roller drive means therein;
   said roller drive means having at least one generally horizontally reciprocating arm pivotally extending therefrom;
   said at least one arm having a roller rotatingly depending therefrom;
   said cabinet further including at least one paving sample tray removably disposed therein and generally beneath said roller of said arm;
   motor means for driving said roller extending from said arm of said drive means reciprocatingly and repeatedly over a paving sample contained within said at least one paving sample tray, for wearing the paving sample;
   a water tank disposed within said cabinet for containing a paving sample water bath therein, with said at least one paving sample tray being removably submersed within said water tank and the water bath therein for exposing the paving sample contained within said sample tray to the effects of moisture; and
   paving sample wear detection means communicating with said at least one reciprocating arm, for measuring deflection of said at least one arm as the paving sample is worn by said roller.

2. The apparatus according to claim 1, wherein said motor means comprises an electric motor driving a speed reduction drive, with said reduction drive turning a crank wheel with a connecting rod extending between said crank wheel and said drive means for converting rotary motion of said crank wheel to linear reciprocating motion of said drive means.

3. The apparatus according to claim 1, wherein said drive means includes two said arms extending therefrom, with each of said arms including a roller rotatingly depending therefrom, and said cabinet includes two said sample trays each disposed generally beneath a corresponding one said roller.

4. The apparatus according to claim 1, including heating means, temperature control means, and circulation control means for the water bath contained within said water tank.

5. The apparatus according to claim 1, wherein said paving sample wear detection means comprises a linear value displacement transducer.

6. The apparatus according to claim 4, including automated lifting means for said at least one reciprocating arm, for automatically lifting said at least one arm when excessive sample wear is detected by said paving sample wear detection means.

7. The apparatus according to claim 6, wherein said lifting means comprises a pneumatic actuation device.

8. The apparatus according to claim 6, including:
   computer control means for controlling said motor means, said heating means, said temperature control means, said circulation control means, and said automated lifting means.

9. The apparatus according to claim 1, including weight means removably installed upon said at least one reciprocating arm for applying a downward compressive force upon said at least one roller and the paving sample disposed therebelow.

10. The apparatus according to claim 1, including emergency shutoff means for at least said motor means.

11. A method of testing paving samples, comprising the following steps:
   (a) providing a fixed, stationary apparatus including at least one powered roller for repeatedly rolling over a corresponding at least one paving sample disposed therebeneath;
   (b) providing a water bath disposed over the paving sample; and
   (c) submerging the paving sample therein for exposing the sample to the effects of moisture
   (d) further providing sample wear detection means for detecting wear of the paving sample as the at least one roller is repeatedly rolled thereover;
   (e) further providing computer means for receiving an output signal from the sample wear detection means, and for recording sample wear according to the received output signal over a period of time;
   (f) reciprocatingly rolling the at least one roller repeatedly across the corresponding at least one paving, sample;
   (g) measuring the wear of the sample due to the at least one roller over a period of time, by means of the sample wear detection means;
   (h) sending the output signal from the sample wear detection means to the computer for processing by the computer; and
   (i) recording the sample wear by means of the computer, for comparing various paving samples tested in accordance with the present method.

12. The method according to claim 11, further including the steps of:
   (a) providing heating means, temperature control means, and circulation control means for the water bath; and
   (b) heating, controlling the temperature, and circulating the water bath respectively by means of the heating means, temperature control means, and circulation control means.

13. The method according to claim 12, further including the steps of:
   (a) providing automated lifting means for at least slightly lifting the at least one reciprocating arm; and
   (b) automatically lifting the at least one reciprocating arm when excessive sample wear is detected by the paving sample wear detection means.

14. The method accosing to claim 13, further including the step of providing a pneumatic actuation device for the reciprocating arm automated lifting means.

15. The method according to claim 13, further including the steps of:
   further providing computer control means for controlling the motor means, heating means, temperature control means, circulation control means, and lifting means; and
   controlling the motor means, heating means, temperature control means, circulation control means, and lifting means in accordance with the computer control means.

16. The method according to claim 11, further including the step of providing a linear value displacement transducer for the sample wear detection means.

17. The method according to claim 11, further including the step of removably applying weight to the at least one reciprocating arm for applying a downward compressive force upon the at least one roller and the paving sample disposed therebelow.

18. The method according to claim 11, further including the step of providing emergency shutoff means for at least the motor means.

* * * * *